(12) United States Patent
Wolf

(10) Patent No.: US 7,964,640 B2
(45) Date of Patent: Jun. 21, 2011

(54) OLIGOMERS OF STRAIGHT-CHAIN AND UNBRANCHED FATTY ACIDS AND DRUGS CONTAINING THESE

(75) Inventor: Hans Uwe Wolf, Neu-Ulm (DE)

(73) Assignee: PLT Patent & License Trading Ltd., Cambridge (GB)

( * ) Notice: Subject to any disclaimer, the term of this patent is extended or adjusted under 35 U.S.C. 154(b) by 220 days.

(21) Appl. No.: 11/995,218

(22) PCT Filed: Jul. 11, 2006

(86) PCT No.: PCT/EP2006/006773
§ 371 (c)(1),
(2), (4) Date: Jul. 14, 2008

(87) PCT Pub. No.: WO2007/006550
PCT Pub. Date: Jan. 18, 2007

(65) Prior Publication Data
US 2009/0012166 A1    Jan. 8, 2009

(30) Foreign Application Priority Data

Jul. 11, 2005    (DE) .................. 10 2005 032 307

(51) Int. Cl.
*A61K 31/19* (2006.01)
(52) U.S. Cl. ............... 514/557; 514/1; 514/560; 554/1; 554/223; 554/224
(58) Field of Classification Search .......... 514/558, 514/560; 554/1, 103, 223, 224
See application file for complete search history.

(56) References Cited

U.S. PATENT DOCUMENTS

| 2,955,121 A | * | 10/1960 | Barrett et al. | ......... 562/509 |
| 3,538,009 A | * | 11/1970 | Kelly et al. | ......... 510/426 |
| 5,545,399 A | | 8/1996 | Lee et al. | |
| 5,753,704 A | * | 5/1998 | Lindner et al. | ......... 514/560 |

FOREIGN PATENT DOCUMENTS

| DE | 4201343 A1 | * | 7/1993 |
| DE | 10305965 A1 | | 8/2004 |
| DE | 103 25 829 A1 | | 12/2004 |
| JP | 63210918 | * | 9/1988 |
| JP | 63-210918 | * | 9/1998 |
| JP | 2004161633 | * | 6/2004 |
| WO | WO 9314060 A1 | | 7/1993 |

OTHER PUBLICATIONS

JP 2004-161633, Matsushita Electric Ind Co Ltd., English Translation (31 pages), Jun. 2004.*
DE 4201343 (A1), Henkel KGAA, English Translation (4 pages), Jul. 1993.*
M. Mao-Qiang et al., "Optimization of Physiological Lipid Mixtures for Barrier Repair", The Journal of Investigative Dermatology, vol. 106, No. 5 (May 1996) pp. 1096-1101.
M. Mao-Qiang et al., "Fatty Acids Are Required for Epidermal Permeability Barrier Function", The Journal of Clinical Investigation, vol. 92 (Aug. 1993) pp. 791-798.
M. Mao-Qiang et al., "Secretory Phospholipase $A_2$ Activity Is Required for Permeability Barrier Homeostasis", J. Invest Dermatol, vol. 106 (1996) pp. 57-63.

(Continued)

*Primary Examiner* — Porfirio Nazario Gonzalez
*Assistant Examiner* — Yate K Cutliff
(74) *Attorney, Agent, or Firm* — Millen, White, Zelano & Branigan, P.C.

(57) ABSTRACT

The present invention relates to new substances which are derived from naturally occurring straight-chain and unbranched fatty acids and also from semi-synthetic and synthetic compounds with principally the same structure in that they represent dimers, trimers, tetramers or higher oligomers of the starting substances.

8 Claims, 4 Drawing Sheets

OTHER PUBLICATIONS

Figure 1:
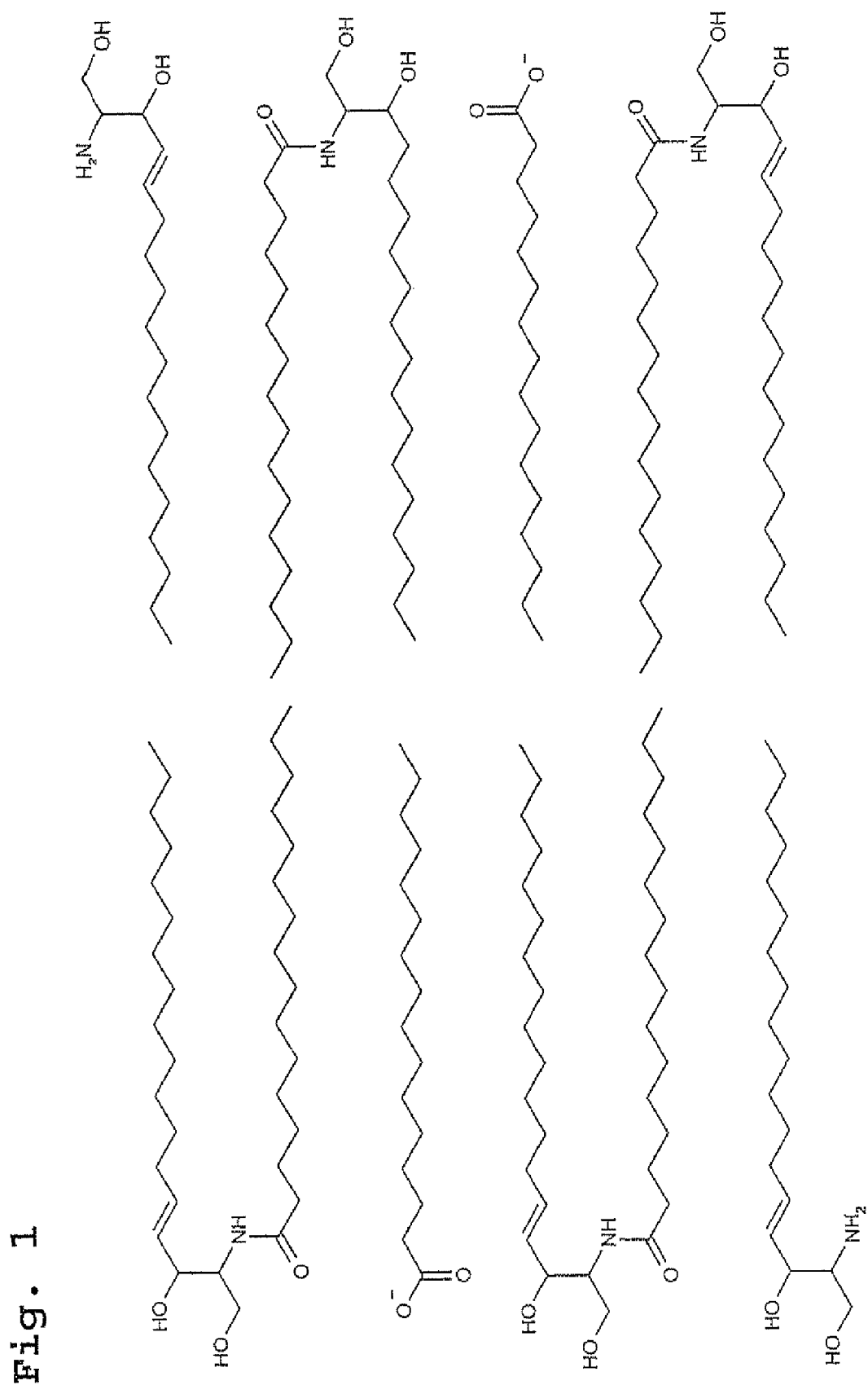

V. Velkova et al., "Influence of the Lipid Composition on the Organization of Skin Lipid Model Mixtures: An Infrared Spectroscopy Investigation", Chemistry and Physics of Lipids, vol. 117 (2002) pp. 63-74.

T.J. McIntosh et al., "X-Ray Diffraction Analysis of Isolated Skin Lipids: Reconstitution of Intercellular Lipid Domains", Biochemistry, vol. 35, No. 12 (Mar. 1996) pp. 3649-3653.

L. Coderch et al., "The Effect of Liposomes on Skin Barrier Structure", Skin Pharmacol Appl Skin Physiol, vol. 12, (1999) pp. 235-246.

J. Arikawa et al., "Decreased Levels of Sphingosine, A Natural Antimicrobial Agent, May be Associated with Vulnerability of the Stratum Corneum from Patients with Atopic Dermatitis to Colonization by *Staphylococcus aureus*", J. Invest. Dermatol., vol. 119 (2002) pp. 433-439.

G. Pilgram et al., "Aberrant Lipid Organization in Stratum Corneum of Patients with Atopic Dermatitis and Lamellar Ichthyosis", J. Invest. Dermatol., vol. 117 (2001) pp. 710-717.

O. Tanno et al., "Nicotinamide Increases Biosynthesis of Ceramides as Well as Other Stratum Corneum Lipids to Improve the Epidermal Permeability Barrier", British Journal of Dermatology, vol. 143 (2000) pp. 524-531.

"Lehrbuch Der Organischen Chemie" (1973)—cited in Examination Procedure of German Priority Application 10 2005 032 307.3.

Database CA [Online] Chemical Abstracts Service, Columbus, Ohio, US, Ono Seigo et al, "Nitroaniline-type nonlinear optical material", XP002404917, Sep. 1988.

Warwel S et al, "Surfactants from Glucamines and Omega-epoxy Fatty Acid Esters", European Journal of Lipid Science and Technology, Wiley VCH Verlag, Weinheim, DE, vol. 103, No. 10, Oct. 2001, pp. 645-654, XP001101948.

Database WPI Week 2005, Derwent Publications Ltd. London, GB; AN 2005-310723, XP002405079.

Database WPI Week 2004, Derwent Publications Ltd. London, GB; AN 2004-521523, XP002405080.

English Translation of DE 103 25 829 A1—"Derivatives of Natural, Semisynthetic and Synthetic Lipids From the Group of Ceramides and Sphingosines, and Use Thereof As Therapeutic Agents in Medicine, Especially in Dermatology", Dec. 30, 2004.

English Translation of "Lehrbuch Der Organischen Chemie" (1973)—cited in Examination Procedure of German Priority Application 10 2005 032 307.3.

* cited by examiner

OLIGOMERS OF STRAIGHT-CHAIN AND UNBRANCHED FATTY ACIDS AND DRUGS CONTAINING THESE

The present invention relates to new substances which are derived from naturally occurring straight-chain and unbranched fatty acids and also from semi-synthetic and synthetic compounds with principally the same structure in that they represent dimers, trimers, tetramers or higher oligomers of the starting substances.

Basically, all biological membranes, in particular cell membranes, contain so-called lipids and lipid-analogous substances as essential components which structurally are constructed differently but which are similar to each other in their construction principle. The similarity in principle of the structure resides in the fact that they are constructed from a hydrophobic and a hydrophilic component.

In the case of lipid-analogous substances from the group of straight-chain and unbranched fatty acids such as for example palmitic acid, the hydrophobic molecule region comprises a fatty acid radical, whilst the hydrophilic component is a carboxyl group.

The amphiphilic structure of the lipid-analogous substances, i.e. the simultaneous presence of a (strongly) hydrophobic and a hydrophilic, polar component of the molecule structure, leads to the lipid-analogous substances in an aqueous phase, generally together with other lipids arranging themselves spontaneously to form a lipid double layer, a so-called "lipid bilayer" which represents inter alia the basis of the structure of biological membranes. The structural principle of this bilayer is the same for all lipids and lipid-analogous substances: they are arranged in two parallel layers which are situated closely together, the hydrophobic radicals of the relevant molecules respectively being situated directly opposite and coming into contact. Hence they form the hydrophobic inner region of the membrane bilayer, whilst the hydrophilic radicals are in contact on both sides of the lipid bilayer with the aqueous phase. The tendency to form this lipid bilayer resides both within and also outwith an organism, e.g. in an aqueous system in which the properties of the lipid bilayers can be examined in experimental arrangements designed specially for this purpose.

Although the structure of the lipid bilayer is formed spontaneously in an organism and has a significant stability, the possibility exists for example in the presence of a lipid metabolism disorder that a biological membrane loses a part of its lipid components because these molecules are formed either too slowly and/or in an inadequate amount or are metabolised (too rapidly) and hence are withdrawn from the membrane structure, the relevant membranes being depleted of the respective components. This leads inter alia to a disorder of the membrane structure and function. A known example of changes of this type is the depletion in the lipid bilayers of the stratum corneum of human skin of fatty acids. It was established in various works that e.g. palmitic acid is a solid component of the stratum corneum and is required for the normal barrier function of the skin (Man M Q M, Feingold K R, Thornfeldt C R, Elias P M (1996): *J Invest Dermatol* 106 (5): 1096-1101; Mao-Qiang M, Elias P M, Feingold K R (1993): *J Clin Invest* 92: 791-798; Mao-Qiang M, Jain M, Feingold K R, Elias P M (1996): *J Invest Dermatol* 106 (1): 57-63; Velkova V, Lafleur M (2002): *Chem Phys Lipids* 117 (1-2): 63-74).

Various skin changes and skin diseases are based on changes in the lipid composition of the stratum corneum layer in human skin. These changes in the lipid composition lead to a more or less greatly changed barrier function of the relevant skin parts for water (McIntosh T J, Stewart M E, Downing D T (1996); *Biochemistry* 35 (12): 3.649-3.653; Coderch L, de Pera M, Perez-Cullell N, Estelrich J, de la Maza A, Parra J L (1999): *Skin Pharmacol Appl Skin Physiol* 12(5): 235-246).

Skin changes and skin diseases of this type are for example:
1. atopic dermatitis
2. "dry" skin xerosis, xeroderma
3. dyshidrotic eczema
4. chronic cumulative toxic contact eczema
5. ageing skin
6. skin severely affected by UV light
7. sebostasis
8. keratinisation disorders In particular in the field of clinical medicine, it is desirable in the mentioned cases of diseases to change and/or to stabilise the structure of the biological membrane present in the organism, i.e. the lipid bilayers, in a suitable manner.

As cited above already, biological membranes of a large number of cells are constructed from a lipid bilayer which represents an effective barrier relative to the extracellular space. This also applies to the stratum corneum of the skin. In humans, this skin structure comprises a plurality of layers of keratinised corneocytes which are embedded in a lipid matrix of a highly ordered lamellar structure. These lipid bilayers essentially contain ceramides, fatty acids, such as e.g. palmitic acid, and also cholesterol.

According to recent knowledge relating to the pathological mechanism of atopical dermatitis (Arikawa J, Ishibashi M, Kawashima M, Takagi Y, Ichikawa Y, Imokawa G (2002): *J Invest Dermatol* 119 (2): 433-439) and related diseases, the cause of the susceptibility of the skin in the case of a disease of this type is inter alia a changed lipid metabolism or reduced lipid content of the stratum corneum. These changes relate inter alia to the fatty acid metabolism. Thus there were revealed, in the case of atopic dermatitis but also in the case of other skin diseases, such as as in psoriasis, in (lamellar) ichthyosis and in contact dermatitis, reduced contents of free fatty acids in the skin of patients (Pilgram G S, Vissers D C, van der Meulen H, Pavel S, Lavrijsen S P, Bouwstra J A, Koerten H K (2001): *J Invest Dermatol* 117 (3): 710-717).

The physiological composition of the membrane lipids of the stratum corneum of human skin is however still of essential importance for the normal structure and function of the skin for a second reason. The presence of an adequate content of these lipids ensures the unrestricted capacity of the skin for binding a physiological quantity of water. The loss of a part of the stratum corneum lipids therefore leads to a restriction in the water binding capacity, the so-called transepidermal water loss of the skin. This is shown in the occurrence of a "dry" and wrinkled skin which frequently but not exclusively occurs in particular in the elderly.

The current possibilities for alleviating the symptoms and consequences of the mentioned skin diseases, in particular atopical dermatitis (at present a cure is still not possible), are still very limited; Topical application of special glucocorticoids and immunosuppressive active substances is associated with significant risks because of the toxicity of these substances. Specific corticoids even cause an almost counterproductive effect in that they lead to a loss of ceramides, cholesterol and free fatty acids.

Taking into account the current state of knowledge about the importance of a physiological lipid composition of the stratum corneum membranes, it is logical to attempt to compensate for any deficits in membrane lipids which exist in the stratum corneum by means of an exogenous supply. In practice, an attempt is made to supply the missing lipids, e.g. free fatty acids, to the changed or diseased skin with the help of ointments, creams and the like. This is effected for example by lipid preparations which are specially formulated for this purpose, including free fatty acids, inter alia by using liposomes. Numerous products have become available commercially in the meantime for the therapy of the mentioned skin diseases.

The therapeutic measures portrayed here should certainly be regarded as correct in principle since they logically attempt to compensate for the deficits existing in the stratum corneum of lipids and lipid-analogous substances. Empirical knowledge established with these therapeutic measures during the last few years reveal however that, despite the correctness of the therapeutic approach in principle, the results of these curative treatments are in no way convincing. In part, the success of the implemented measures is unreliable. Even if an approximately acceptable success of the curative treatment arises, a curative treatment of this type has at least two serious disadvantages:

The extent of the successful cure is not so great that it can be called complete recovery of the diseased skin.

In order to ensure to some extent an acceptable successful cure of the skin over a fairly long period of time, the mentioned lipids and lipid-analogous substances must be supplied permanently to the skin at short time intervals.

Both disadvantages can be attributed to a common cause. The mentioned free fatty acids are not static components of the skin but are intermediate products of a reaction sequence in which the free fatty acids required by the skin are released e.g. from nutritional fats (triglycerides), from ceramides or phospholipids and, after their release with detection of their function as membrane component of the stratum corneum, are subsequently included in the oxidative fatty acid metabolism.

This reaction sequence represents a steady state in which a specific quantity of the mentioned components is changed metabolically by the effect of specific enzymes step by step. Hence a specific throughput of substance occurs. The fatty acids supplied exogenously as skin therapeutic agents are included in this reaction sequence. If there is a priori a disruption in this reaction sequence which then leads to a pathological lipid composition of the stratum corneum, then it is to be expected that the exogenous supply of lipids in the form of a therapeutic agent can fundamentally change nothing or not much in this pathological state since the exogenously supplied fatty acid component of the organism is further processed in the same way as is the case with the fatty acid component made available endogenously. A successful cure with the therapeutic possibilities available at present is therefore dependent to a large extent upon the relevant therapeutic replacement substances being able to penetrate into the skin more rapidly than they are included in the existing physiological degradation steps and them being supplied continuously over a fairly long period of time, in the extreme case for life.

The present problem cannot be readily resolved. Certain physiological and physical-chemical or biochemical limits are set upon the rate of absorption of lipids and lipid-analogous substances into the stratum corneum, for example with respect to the diffusion rate of the therapeutic agents. This rate cannot be increased arbitrarily. On the other hand, the lipid-degrading enzymes which are involved in the mentioned reaction sequences cannot be influenced by exogenous measures or not without serious problems in the sense of reducing their activity.

The complementary therapeutic approach, i.e. the activation of lipid-synthesising enzymes by exogenous active substances (e.g. nicotinamide) is only possible to a limited extent and has been achieved to date only in vitro (Tanno O, Ota Y, Kitamura N, Katsube T, Inoue S (2000): *British J Dermatol* 143 (3): 524-531).

In order to resolve the described problem, it is necessary basically to apply other principles in order to increase the therapeutic effectiveness of exogenously supplied lipid replacement substances or lipid-analogous substances.

The object of the present invention is therefore to provide compounds by means of which biological membranes present in the organism can be modified and/or stabilised.

This object is achieved with respect to the described oligomers by the features of patent claim 1, with respect to the human or veterinary drug by the features of claim 18, with respect to the cosmetic or body care agent by the features of claim 19 and with respect to the use as a drug by the features of claim 20. The further dependent claims reveal advantageous developments.

There is understood by oligomers in the sense of the invention the cross-linking of two to twelve monomers. There are preferred here in particular dimers, trimers, tetramers, pentamers, hexamers and octamers.

The term "dimerisation" is used according to the present invention also when not only is the direct covalent cross-linking of two molecules involved with doubling of the number of the respectively contained atoms but also when the two original individual molecules are connected by a short molecular bridge in the sense of a so-called spacer. According to the present invention, the term "oligomers" is also used when these compounds involve not only a plurality of covalent cross-linked molecules but also when the monomers are connected by molecular bridges in the form of different spacers.

The structural elements of the lipid-analogous substances thereby preferably comprise the group of fatty acids from palmitic acid or from other monocarboxylic acids with a chain length between 10 and 40 C-atoms. Preferably, the fatty acids are selected from the group comprising n-hexadecanoic acid (palmitic acid, $C_{15}H_{31}$—COOH), n-dodecanoic acid (lauric acid, $C_{11}H_{23}$—COOH), n-tetradecanoic acid (myristicinic acid, $C_{13}H_{27}$—COOH), n-octadecanoic acid (stearic acid, $C_{17}H_{35}$—COOH), n-icosanoic acid (arachidic acid, $C_{19}H_{39}$—COOH), n-tetracosanoic acid (lignoceric acid, $C_{23}H_{47}$-COOH), 9-hexadecenoic acid (palmitoleic acid, $C_{15}H_{29}$—COOH), 9-octadecenoic acid (oleinic acid, oleic acid, $C_{17}H_{33}$—COOH), 9,11-octadecadienoic acid ($C_{17}H_{31}$—COOH), 9,12-octadecadienoic acid (linolic acid, $C_{17}H_{31}$—COOH), 9,12,15-octadecatrienoic acid (linolenic acid, $C_{17}H_{29}$—COOH), 5,8,11,14,17-icosapentaenoic acid ("EPA", $C_{19}H_{29}$—COOH), 4,7,10,13,16,19-docosahexaenoic acid ("DHA", $C_{21}H_{31}$—COOH), decanoic acid ($C_{10}H_{21}$—COOH), octacosanoic acid ($C_{28}H_{57}$—COOH) and 9-octacosenoic acid ($C_{28}H_{55}$—COOH).

The compounds according to the invention must fulfill the following requirements:

1. The fatty acids forming the oligomers must concern straight-chain and unbranched compounds.
2. The oligomerisation must take place with formation of exclusively covalent bonds between the individual fatty acids.
3. The basic structure of the lipid or lipid-analogous substances used which enables the formation of the lipid double membrane, should not only stay maintained but the capacity to form the double membrane should be increased because the skin damaged by the mentioned diseases in any case has only a restricted capacity to synthesise and to maintain the physiological lipid double membrane.

4. The structure of the lipid or lipid-analogous substances which are used should be changed keeping the basic structure to such an extent that they can still function only to a lesser extent as substrates for the enzymes present in the skin, especially in the stratum corneum. This means that they are intended to be included to a significantly lesser extent than the original lipids or lipid-analogous substances in the respective enzymatic reaction sequences and hence should stay maintained as essential structural components of the stratum corneum over a longer period of time than the original lipids or lipid-analogous substances.

5. The alteration in the molecular structure should however be effected only to such a small extent that such substances as are produced by the low metabolism-related conversion or degradation of the supplied oligomeric additional lipids are similar as far as possible to the intrinsic body lipids or lipid-analogous substances. In this way, the danger is significantly reduced that metabolic products with a toxic effect are produced.

The synthesis of a molecular structure, which fulfils the three above-indicated requirements, resides firstly in a dimerisation of the fatty acids used for the anticipated therapeutic effect.

Because of the structural asymmetry of the entire group of fatty acids—on one hand the fatty acid radical(s) as hydrophobic structural component (termed "tail" in English language usage) and, on the other hand, the hydrophilic radical, in the form of the carboxyl group (termed "head" in English language usage)—three different types in principle can be differentiated, for example, two monomeric fatty acid molecules can be bonded covalently to form a dimeric molecule:

1. in the form of a "tail-to-tail" arrangement, i.e. by covalent cross-linking between the hydrophobic fatty acid radicals of the two molecules to be connected. This cross-linking is effected for example by the incorporation of a so-called intramembrane spacer.
2. in the form of a "head-to-head" arrangement, i.e. by covalent bonding between the two hydrophilic, polar carboxyl groups of the two fatty acid molecules to be connected. This cross-linking is effected for example by the incorporation of a so-called extramembrane spacer.
3. in the form of a "head-to-tail" arrangement, i.e. by covalent bonding between the carboxyl group of the one fatty acid molecule and the hydrophobic fatty acid radical of the second fatty acid molecule.

Variant 1, i.e. the tail-to-tail arrangement, is based on the cross-linking preferably of the respectively $\omega$-position carbon atoms of the fatty acid radicals of both molecules to be connected, i.e. with the help of a spacer. A spacer of this type can be termed "intradimeric" spacer, on the one hand, because of the cross-linking of two monomers to form one dimer. Since this spacer is disposed in the membrane interior during storage of the dimer in the biological membrane, it is however termed preferably "intramembrane" spacer. The terms intradimeric and intramembrane should therefore be considered as equivalent with respect to their meaning.

This intramembrane spacer must have a hydrophobic nature since it is located in the hydrophobic inner region of the biological membrane. Hence a dimeric molecule is present which, because of the arrangement of its hydrophobic molecular region in the interior of the dimer, can be integrated without difficulty into a biological lipid bilayer. FIG. 2 shows the type of cross-linking and the similarity of the dimerisation product with the physiological structure of the lipid double membrane in the example of two cholesterol molecules (cf. FIG. 1).

Figure 2:
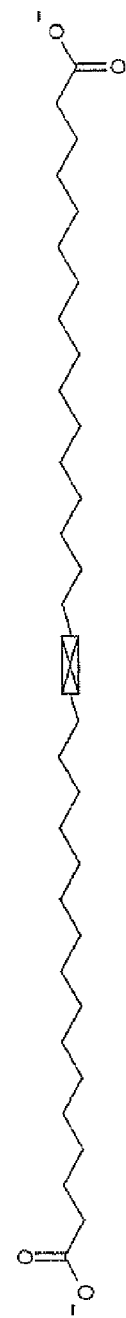

The tail-to-tail arrangement represents direct imitation of the stable arrangement of the fatty acids which is naturally present in biological membranes, as can be detected by comparison with the arrangement of the components in FIG. 1. The tail-to-tail dimer should be regarded as one of two possible basic structures for the entirety of all further lipid oligomers described here.

The dimerisation of the fatty acids by means of cross-linking via an intramembrane spacer hence leads to molecules which are inserted not only in the structure of a lipid double membrane without difficulty but which, furthermore, as a result of the presence of a covalent cross-linking between the $\omega$-position C-atoms of the fatty acid radicals of two oppositely situated fatty acid molecules, also contribute to significant structural stabilisation of the lipid double membrane.

Variant 2, i.e. the head-to-head dimer, has a structure which does not permit integration of the molecule into only one single lipid bilayer because the hydrophilic region of this dimeric molecule would be disposed in the hydrophobic interior of the membrane bilayer, which would represent an extremely unstable structure which consequently is not formed spontaneously. The head-to-head dimers have however in this respect biological or medical importance in that the two fatty acid molecules which are cross-linked in this manner can be anchored in two lipid bilayers which are disposed parallel at a close spacing, each of the two monomers being located in respectively one half of the two parallel lipid bilayers. Such lipid bilayers which are disposed at a close spacing occur for example in the myelin sheath of nerve cells.

Figure 3:
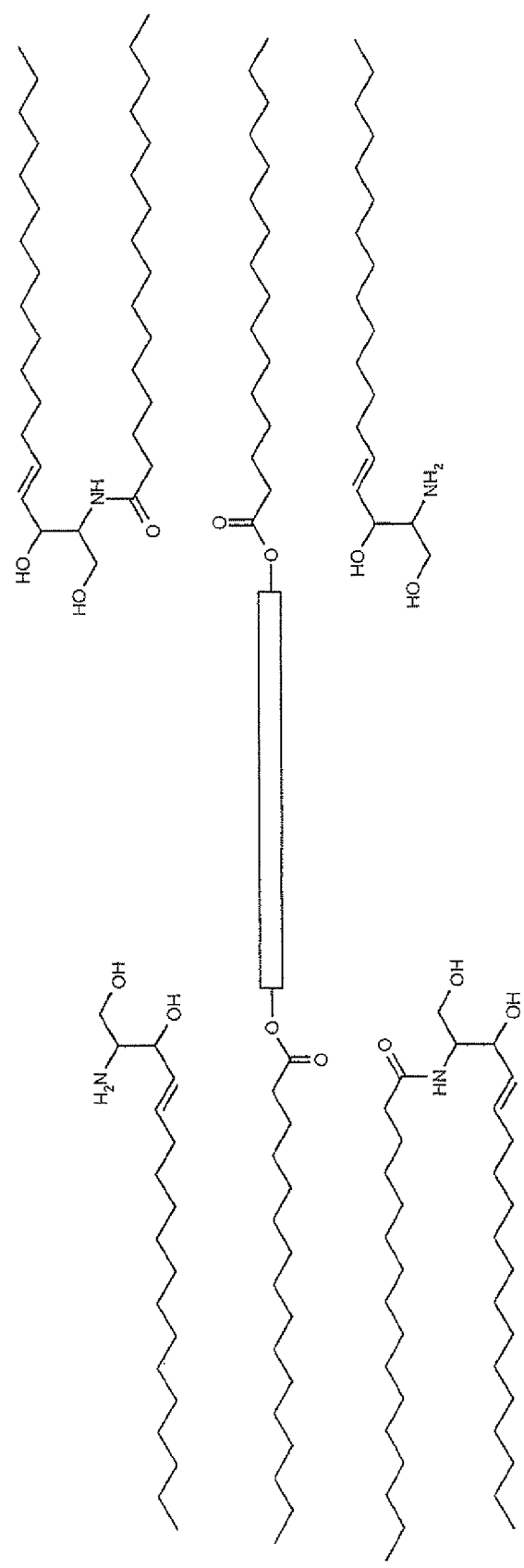

In the case of the "head-to-head" fatty acid dimer, it can be however be necessary for spatial reasons to incorporate a so-called spacer (with variable chain length) between the two monomers in order to make possible integration of the two lipid components into the two lipid bilayers even when these bilayers have a specific spacing from each other (see FIG. 3 in this respect). This applies for example in the case of the lipid bilayers of the stratum corneum of human skin which are disposed parallel.

However it should be assumed that such a molecule is not yet integrated optimally in two parallel-disposed lipid bilayers. Optimal integration is achieved by a molecule, in the case of which two dimers (instead of the two monomers) are cross-linked with each other, said dimers then being integrated in the two parallel-disposed biological membranes. This (tetrameric) molecule then has the following structural features (see FIG. 4 in this respect):

The two dimers are constructed respectively from the monomers in the tail-to-tail arrangement by cross-linking with the help of the above-mentioned intramembrane spacer. The cross-linking of the two dimers is effected in the head-to-head arrangement via a further spacer which can be termed interdimeric spacer because it is disposed between two preformed dimers. Since it is located outwith the two membranes after integration of the entire molecule, it is however termed advantageously extramembrane spacer. The two terms of interdimeric and extramembrane can therefore be equated in meaning.

The extramembrane spacer, because of its position outwith the membrane, i.e. in the hydrophilic extramembrane region of the cell, must have a hydrophilic structure.

Variant 3 of the lipid dimerisation has practically no biological or medical importance since a molecule of this structure (without or with spacer) cannot be integrated in any way into one or two parallel-disposed biological lipid bilayers. In all cases, at least in part hydrophilic structural components of the dimer would require to be integrated into hydrophobic regions of the membranes, which would lead, as known, to very unstable structures which cannot be formed spontaneously for this reason.

Furthermore, the invention includes the possibility of producing hybrid molecules e.g. comprising respectively one molecule of palmitic acid and one molecule of another saturated or unsaturated fatty acid or comprising two molecules of the mentioned fatty acids according to claim 3 and of using them in the manner described below for therapeutic purposes.

As a result of the dimerisation and particularly as a result of the oligomerisation, it is ensured that a molecule of this type is degraded or converted very much more slowly by the enzymes of the fatty acid metabolism which are present in the skin than applies to the corresponding monomeric fatty acids. The enlargement of the fatty acid molecule associated with dimerisation or oligimerisation leads to a severe reduction in the enzymatically controlled metabolisation because, in the case of the known high substrate specificity of most enzymes, the change in size of a substrate by the factor of at least 2 can allow the speed of the substrate conversion to fall considerably.

On the other hand, the resulting reaction products are so similar with respect to their general construction to naturally occurring molecules of the fatty acid metabolism that inclusion in the corresponding reaction sequences is possible without difficulty. Furthermore, it does not require in any way to be taken into account that the dimerised or oligomerised fatty acid molecules have relevant toxicity because of the great similarity to physiologically occurring molecule species.

A specific degree of physiological degradability of the fatty acid dimers and oligomers which should be regarded however as significantly less than that of the monomeric fatty acid molecules is hence a desired property of the molecule for pharmacokinetic and pharmacological reasons because, as a result, the controllability of the therapy is ensured more than if no more metabolic degradation at all were possible.

In the case where the products produced from the fatty acids by cross-linking of the two ω-position C-atoms of the fatty acid radicals have too low a metabolic degradability, sufficiently high degradability can be achieved and ensured in that a quasi "metabolic predetermined breaking point" is introduced into the above-mentioned intramembrane spacer, said spacer comprising one or more C-atoms in combination with one or more O- or N-atoms (FIG. 2).

In the simplest case, this spacer can comprise at least one heteroatom, such as e.g. oxygen or nitrogen, in combination with a C-atom. Preferred chain lengths for the intramembrane spacer are 1-4 atoms.

During synthesis of such a "head-to-head" dimer, the operation cannot start from the original fatty acid molecules but from the ω-hydroxy derivatives, i.e. of the ω-hydroxypalmitic acid. The dimerisation via the ω-position carbon atom does not lead here to a pure hydrocarbon chain, as shown in FIG. 2a, but to an oxygen bridge with water production.

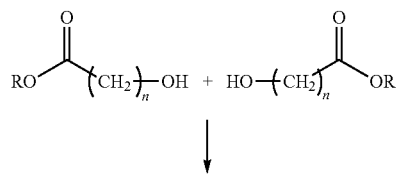

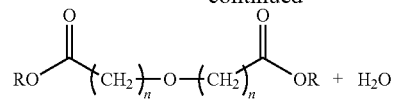

The now produced dimeric molecule contains an oxygen atom at the bridge point. The carbon atoms which are in the direct vicinity (the original ω-C-atoms) can be enzymatically hydroxylated, for instance by the cytochrome-$P_{450}$-dependent mixed-functional hydroxylases. A hydroxylation of this type taking place in the direct vicinity of the O-atom leads to the formation of unstable compounds with a semi-acetal structure which degrade into the corresponding reaction products. The one reaction product with a ω-position OH group is identical to the starting product ω-hydroxypalmitic acid. The other reaction product is a fatty acid with a ω-position aldehyde function which is further oxidised to form the carboxylic acid group. Hence it becomes obvious that, by means of a (slowly proceeding) biochemical degradation of the described dimeric and finally also the oligomeric molecules, in part the physiological starting compounds themselves are produced or molecules which are constructed at least very similarly to the starting compounds.

In the case where the dimerisation of the two fatty acid molecules is intended to lead at the same time to a controllable degree of degradability of the resulting dimeric molecule or/and where—for instance for steric reasons—the resulting dimeric molecule is intended to have a longer chain than corresponds to the sum of the chain lengths of the monomeric molecules, a longer intramembrane spacer can be incorporated between the two fatty acid radicals. This is achieved for example by the use of glycols, in the simplest case ethylene glycol, for bridging the ω-hydroxy fatty acids. In this case, a reaction product is produced which contains two oxygen atoms in the entire chain:

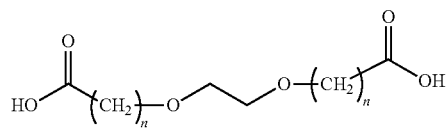

Hence the entire molecule has grown relative to the sum of the two monomeric molecules in practice by the length of the intramembrane spacer —O—$CH_2$—$CH_2$—O—. Because of the two oxygen atoms present in this chain, a controllable degradation rate of the dimeric and hence also of the oligomeric molecule is provided as a result of the ability of the C-atoms adjacent to the O-atoms to be oxidised, if necessary by means of additional variation of the spacer structure.

In this way, due to the choice of a suitable intramembrane spacer, both the entire size of the resulting dimeric molecule and the extent of its biochemical degradability can be chosen freely because it is possible to incorporate so-called "metabolic predetermined breaking points" in the intramembrane spacer. However it must be ensured that an intramembrane spacer should have no pronounced hydrophilic properties since otherwise the possibility of integration of the dimer into the lipid double membrane can be reduced.

An essential aspect of the pathogenesis of the above-mentioned skin changes or skin diseases is the reduced water binding capacity of the skin tissue, in particular in the region of the stratum corneum. Physiologically, the water is not incorporated within, but rather in the space between, the individual lipid bilayers, since a plurality of parallel-disposed lipid layers is present. This is based on the fact that the interior of the lipid bilayer is constructed from strongly hydrophobic fatty acid esters, whilst the medium outwith the lipid bilayer is of a hydrophilic nature. Storage of water in the hydrophobic inner regions of the lipid double membrane is not possible in practice.

The initially mentioned skin changes and diseases are ultimately attributable to the loss of a part of the parallel-disposed lipid bilayers and the hydrophilic intermediate layers disposed between these bilayers and also of water. The aim of the therapeutic measures in these diseases is hence not only reconstruction and stabilisation of the lipid bilayers themselves, as is effected with the help of the above-described dimers of various fatty acids but, in addition, also the construction and stabilisation of the multilamellar lipid structures with the hydrophilic intermediate layers which are situated therebetween and are of crucial importance for the water binding capacity of the skin.

This aim is achieved in that at least two of the above-mentioned "tail-to-tail" fatty acid dimers are cross-linked covalently. In contrast to the above-described formation of dimeric fatty acid molecules by producing a covalent bond in the hydrophobic region of the molecule, i.e. at the ω-position C-atom of the fatty acid chain, the covalent bonding of two fatty acid dimers is effected according to a different principle:

1. The cross-linking of two fatty acid dimers is effected at the hydrophilic ends of the relevant molecules. As the illustration of the example of palmitic acid in FIG. 1 shows, a COOH group is respectively available at the hydrophilic end of the molecule, on which the synthesis of larger molecules, comprising at least two fatty acid dimers, can be effected.
2. Cross-linking of two fatty acid dimers is effected not directly which would technically be possible with water production by forming an (although unstable) acid anhydride grouping. Rather it is necessary for physiological reasons to have an intermediate space produced of a defined minimum size between respectively two forming parallel-disposed lipid layers, in which space water and possibly hydrophilic molecules, possibly also the comparatively large molecule collagen, can be stored. The construction of an intermediate space is however possible, as already mentioned earlier, if and only if the two fatty acid dimers to be cross-linked are kept at a spacing by an extramembrane spacer (FIG. 3).

For the above-mentioned reasons—the intermediate space produced by the spacer between two parallel-disposed lipid bilayers should be able to absorb and store water and hydrophilic molecules—the extramembrane spacer must always have hydrophilic properties. However it can be provided according to the present above-mentioned skin disease with a greatly different chain length.

In the following, some examples of structures of extramembrane spacers are intended to be indicated, in the case of which respectively one hydrophilic molecule structural element with a different structure and chain length is cross-linked with the COOH group which is present respectively at the hydrophilic end of the fatty acid molecule (in the following examples, in addition respectively the subsequent CH$_2$ group of the two fatty acid components is indicated):

With glycerine as spacer-forming molecule, the following structure of the extramembrane spacer is produced with two ester groupings:

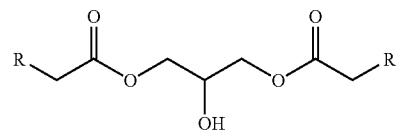

The additional incorporation of one or two arbitrary amino acids, such as e.g. aspartic acid, leads, with formation of two peptide bonds and two ester groupings, to an extended strongly hydrophilic spacer because of the presence of two free dissociated carboxyl groups:

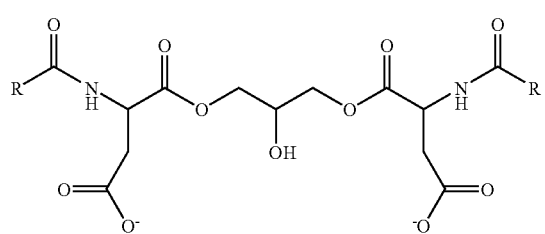

When using two molecules of serine, with formation of four ester groupings, an extended spacer is produced which is also strongly hydrophilic because of the presence of two amino groups which can be protonated at physiological pH values:

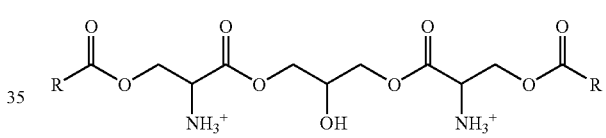

The synthesis of a urea derivative as structural element of the extramembrane spacer is of particular interest. This is possible by the use of two molecules of a basic amino acid, such as e.g. lysin. A relatively long spacer is hereby produced which has a strongly hydrophilic nature, which is provided inter alia by the presence of the two negatively charged carboxyl groups:

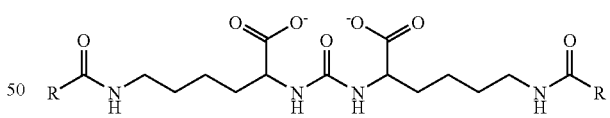

The synthesis of a urea-similar structure is therefore of particular interest because urea has a very high water binding capacity which is used today already in the form of urea-containing ointments for the therapy of such skin diseases in which drying of the skin represents an essential feature of the disease (e.g. in the case of dyshidrotic eczema).

There are in practice no limits on the diversity of the spacer structures and the length of the usable spacers. The structure just as the chain length can be varied widely as necessary to the special therapy demands. The incorporation of specific monosaccharides, such as e.g. glucose, is also possible inter alia, which leads in turn to derivatives of physiological substances.

The choice of the mentioned different structures in the interdimeric spacer leads to different biological stabilities and hence to a different degree of the desired degradability of the oligomeric fatty acid molecule, which is intended on the one hand to be significantly below the value for the monomeric fatty acid molecules but, on the other hand, is intended not to be entirely missing. Hence a certain controllability of the effective strength and duration of the fatty acid oligomers which are used for the therapy is also provided via this intermolecular spacer structure.

Also in the case of the metabolic degradation of the described oligomeric fatty acid molecules, in particular the spacers thereof, degradation products are produced which are identical to physiological substances (e.g. amino acids+monomeric fatty acids) or have very great similarity to them so that the probability of undesired side-effects, in particular toxic effects, is extremely low.

Relative to the dimeric fatty acid molecules, ologomeric molecules with 2-12 monomers, in particular tetramers, hexamers or octamers, have a greater capacity to stabilise the structure of the parallel-disposed lipid membrane bilayers. Due to these compounds, the result is the construction or stabilisation of 2 parallel-disposed bilayers in the case of tetramers, of 3 parallel-disposed bilayers in the case of hexamers, of 4 parallel-disposed bilayers in the case of octamers etc., with an increased tendency towards storage of water and hydrophilic molecules of the most varied of sizes in the spaces between the parallel lipid bilayers.

Oligomeric fatty acid molecules with an uneven number of molecules, in the simplest case i.e. a trimeric molecule with an intramembrane and an extramembrane spacer, can certainly be used also for the purposes mentioned here even if they do not have the optimal properties for integration in the present lipid bilayers. In the example of a trimeric fatty acid molecule, the two fatty acid molecules connected via an intramembrane spacer would be integrated optimally into a lipid bilayer, whilst the further fatty acid molecule connected via an extramembrane spacer would merely protrude into the one half of the next lipid bilayer.

A fatty acid dimer represents a special case, which is connected via an extramembrane spacer (according to the above-indicated "head-to-head" variant of the cross-linking during fatty acid dimerisation). It also applies to this molecule that it can be used perfectly well for the purposes mentioned here even if it has the optimal properties for integration into the present lipid bilayer even less. In this case, both present fatty acid molecules protrude merely into one half of the respectively adjacent lipid bilayers.

The invention is explained subsequently in more detail with reference to the Figures and Examples. However these are not intended to restrict the present invention to the embodiments shown here.

FIG. 1 shows the arrangement of a free fatty acid in a typical stable structure of the lipid bilayer of biological membranes. The hydrophobic fatty acid radicals are directed into the interior of the membrane, and there form a hydrophobic region. The hydrophilic polar radicals are orientated outwards in the direction of the aqueous phase, i.e. of the adjacent intra- or extracellular liquid.

FIG. 2 shows the coupling according to the invention of two straight-chain, unbranched fatty acids to form a dimer by cross-linking with an intramembrane spacer (rectangle).

FIG. 3 shows, in schematic representation, the arrangement of a "head-to-head" dimer according to the invention of two straight-chain, unbranched fatty acids by cross-linking with an extramembrane spacer. The dimer is anchored with respectively one monomer in respectively one half of two parallel-disposed lipid bilayers. The rectangle between the two monomers represents the so-called extramembrane spacer. Only one half of the two adjacent double membranes respectively is represented.

Figure 4:
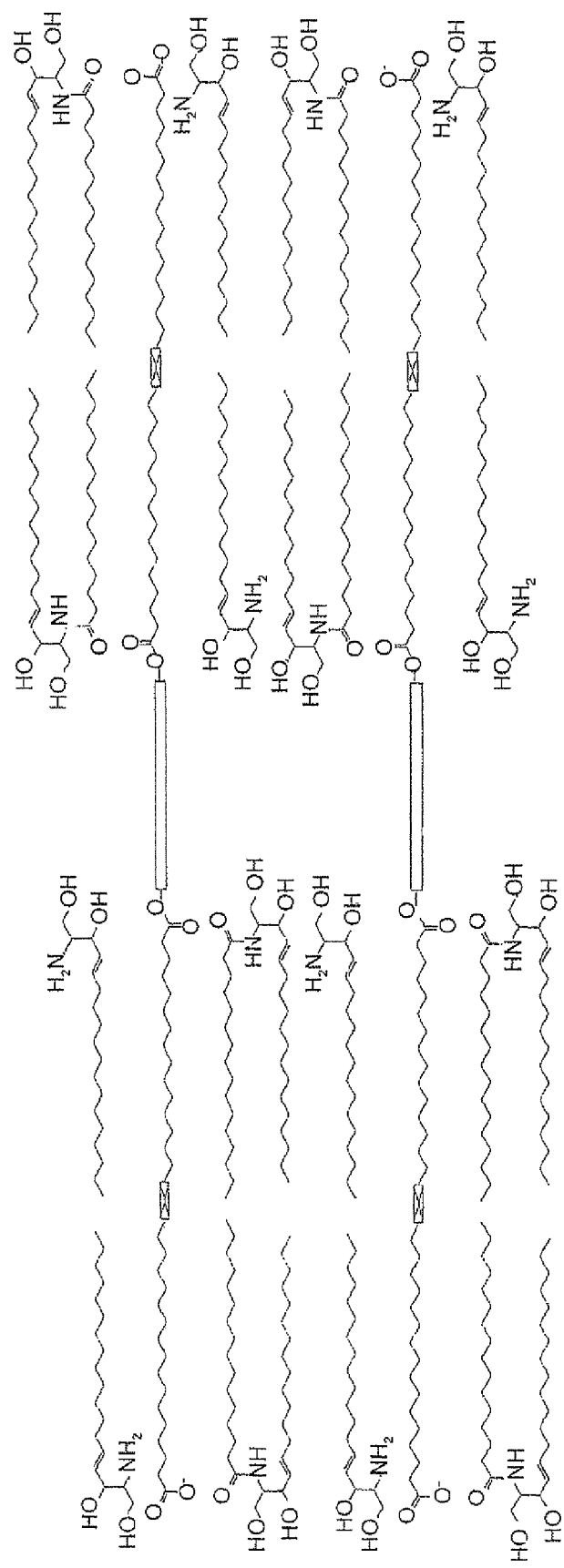

FIG. 4 shows, in schematic representation, the arrangement of tetrameric molecules according to the invention, which function as connecting element between two lipid bilayers. Between the two adjacent lipid bilayers there is a hydrophilic intermediate space. The two dimers constructed in the "tail-to-tail" arrangement, which are in the interior of the membrane, are connected by an intramembrane spacer. The two dimers themselves are cross-linked via an extramembrane spacer which is located in the hydrophilic intermediate space of the two membranes.

Analogously to the tetrameric compounds shown in FIG. 4, hexamers according to the invention can be stored in a similar manner in three lipid membranes which are separated from each other, octamers in four lipid membranes etc.

Fatty acid oligomers of the described type can be applied in medicine for therapeutic purposes wherever the natural construction of biological membranes is disturbed by pathological processes and, by the use of these oligomeric compounds, stabilisation of the membrane structure and/or a change in the membrane properties is intended to be achieved in the sense of a therapeutic goal (e.g. in order to increase the membrane stability).

A few examples are mentioned subsequently:

In the case of specific poisonings, which preferentially affect the liver, such as e.g. poisoning with tetrachloromethane (tetrachlorocarbon, "TETRA", $CCl_4$), the lipids of the liver cell membranes are attacked in their structure by radicals. During this process, the fatty acid radicals of the lipids are oxidised, as a result of which the carbon chain is degraded after a series of different reactions. The consequence thereof is partial degradation of the lipids and destabilisation of the membrane which leads to partial dissolution of the cell membrane and hence to severe damage to the cell. The supply of the described compounds according to the invention, in the present case of fatty acid dimers, can contribute in such a case of poisoning to significant stabilisation of the membrane of the damaged liver cells.

A change in the lipid composition of nerve cells occurs in the case of a large number of different cases of pathological damage to nerve cells. There are associated herewith inter alia neuronopathy, axonopathy and myelinopathy. As causes for the damage or the degradation of the lipid-rich myelin sheaths, there applies inter alia the effect of exogenous harmful substances.

In the case of myelinopathies, such as for example multiple sclerosis, there are considered for stabilisation of the lipid membranes of the myelin sheaths, because of their specific structure, preferably oligomers of the mentioned fatty acids both with short hydrophobic intramembrane and with short hydrophilic extramembrane spacers.

In several tests, it could be detected to date that the presence of ω-3-multiply-unsaturated fatty acids in lipids has an antithrombotic effect. The background to this effect is obviously the preferred storage of this lipid species in the membranes of blood cells, in particular in membranes of the blood platelets, relative to those of the lipids with ω-6-multiply unsaturated fatty acids. The application of fatty acid oligomers with a high content of ω-3-multiply-unsaturated fatty acids is possible in particular in those cases in which a genetically determined fat metabolism disorder leads to a high thrombotic, atherosclerotic and cardiovascular risk.

According to the present state of knowledge, skin diseases are one of the main areas for use of the mentioned fatty acid oligomers, not least because, in the stratum corneum of human skin, straight-chain, unbranched fatty acids, in particular palmitic acid, play an essential role.

The mentioned compounds can be synthesised for example via the following paths:

1. Dimerisation with an Intramembrane Spacer

The intramembrane spacer, because of its position in the interior of the biological membranes, must have predominantly hydrophobic properties. It has the following general structure:

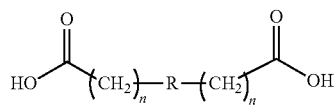

R=O, N, —O—$(CH_2)_x$—O— x=1-30

In the case of oligomers with more than 2 fatty acids R can also be =—$(CH_2)_y$— with y=1-30

Examples of Synthesis Paths

1.1 Condensation of Two ω-Hydroxycarboxylic Acid Esters with Subsequent Ester Cleavage

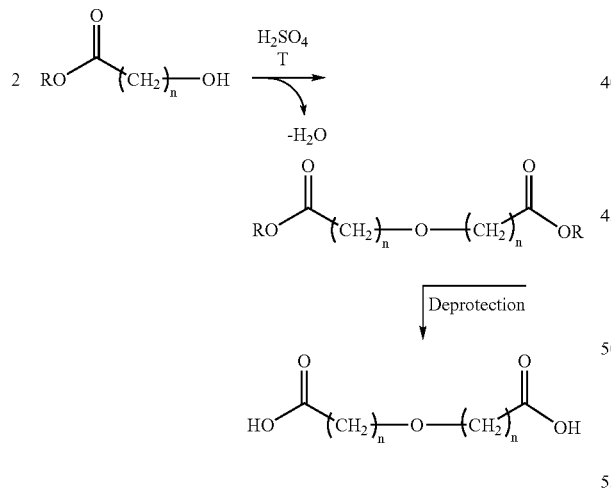

1.2 Ether Synthesis with ω-Hydroxycarboxylic Acid Esters and ω-Halogencarboxylic Acid Esters with Subsequent Ester Cleavage

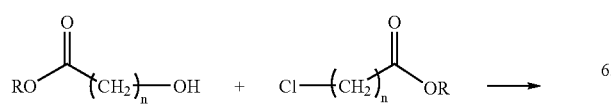

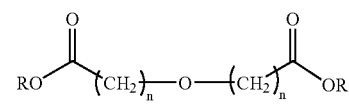

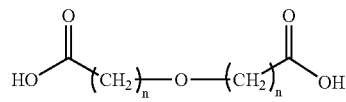

In the case of oligomers with more than 2 fatty acids R can also be =—$(CH_2)_y$—. Then there are the following synthesis possibilities:

1.3 C—C Cross-Linking of Two ω-Halogencarboxylic Acid Esters with Subsequent Ester Cleavage

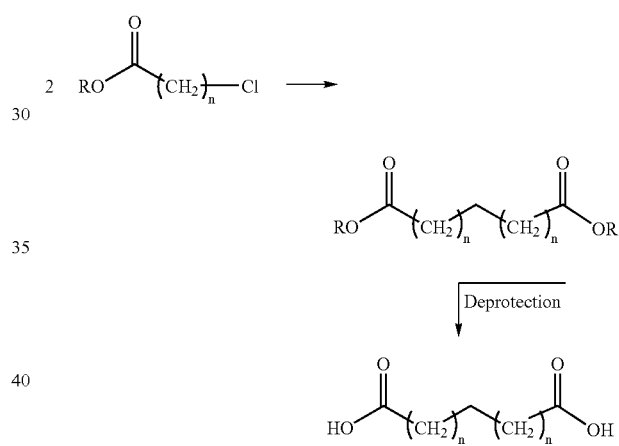

1.4 C—C Cross-Linking of Two ω-Aldehyde Carboxylic Acids with Subsequent Deprotection

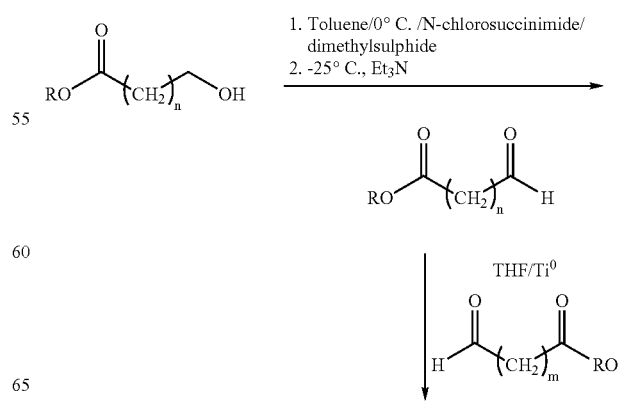

15

-continued

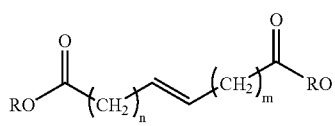

↓ Deprotection

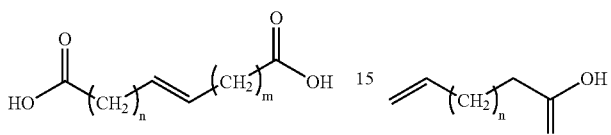

1.5 C—C Cross-Linking with Respectively Subsequent Reaction to Form Dicarboxylic Acid

1.5.1 C—C Cross-Linking of Two ω-Halogen-1-Alkenes

1. Mg/Ether
2. Br—(CH₂)ₘ—CH=CH₂
3. Li₂CuCl₄/THF

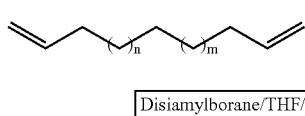

↓ Disiamylborane/THF/H₂O
NaOH/H₂O₂

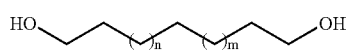

↓ CrO₃/H₂SO₄

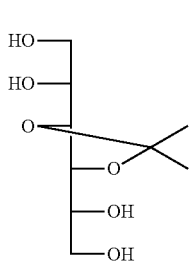

Tos.-chloride/
pyridine
→

16

-continued

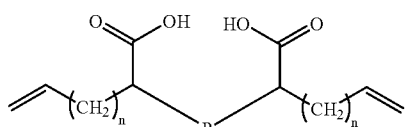

1.5.2 C—C Cross-Linking of Two Carbon-ω-en-Acids with 1,ω-Dibromoalkane

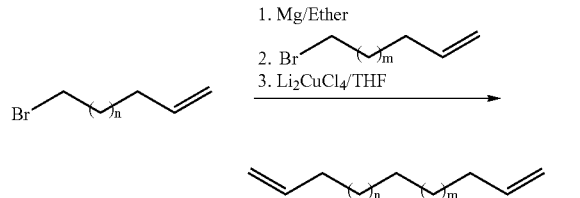

↓ Barton decarboxylation

↓ Disiamylborane/THF/H₂O
NaOH/H₂O₂

↓ CrO₃/H₂SO₄

1.5.3 Illustration Via ω-Hydroxy-1-Alkenes or ω-Halogen-1-Alkenes with 3,4-O-Isopropylidene-D-Mannitol

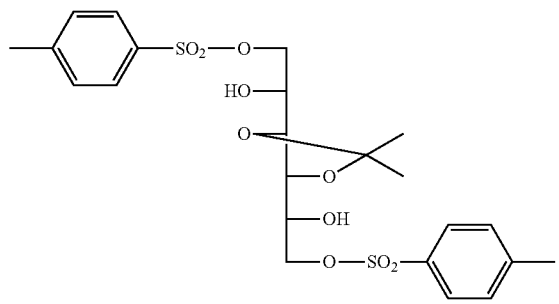

↓ K₂CO₃/MeOH

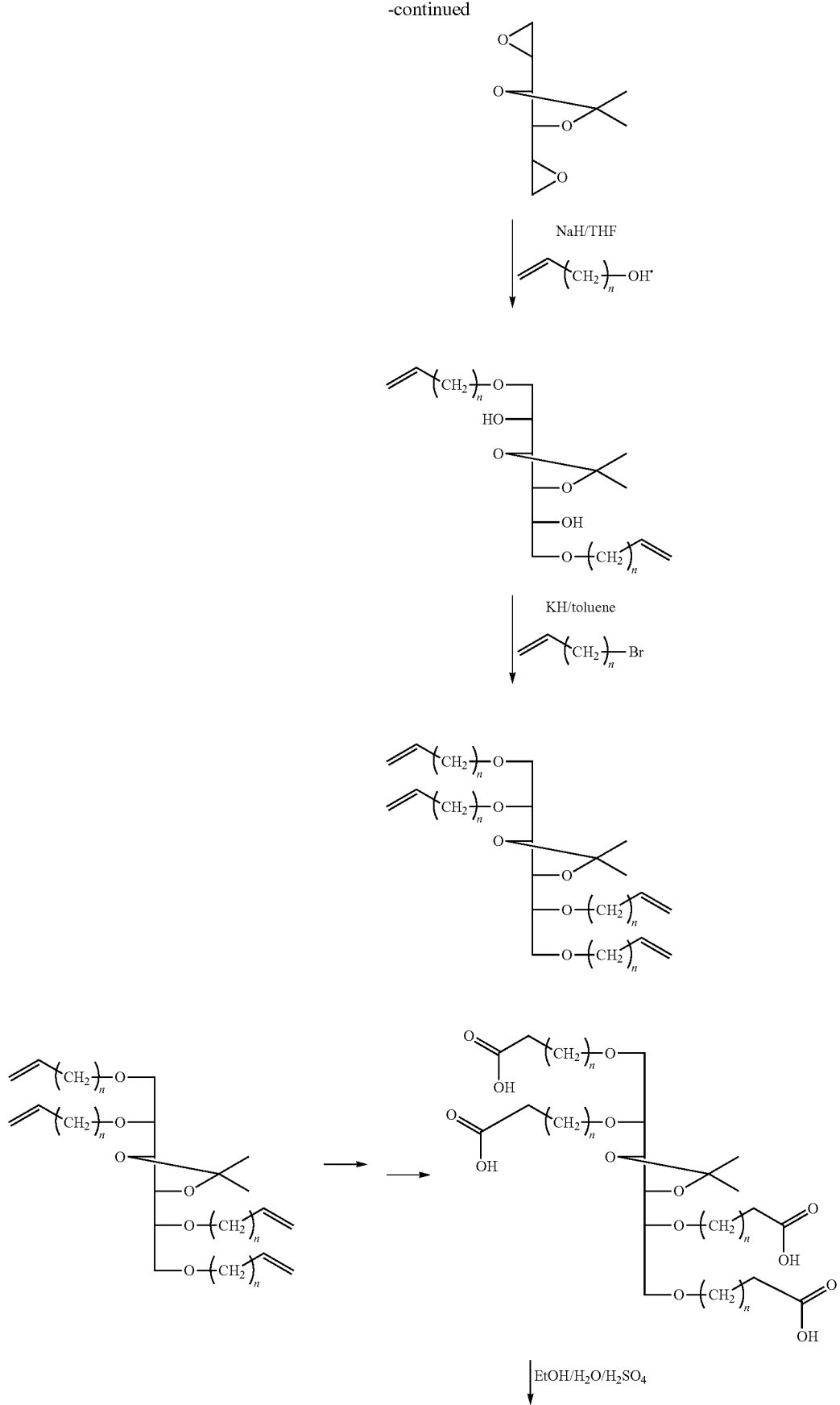

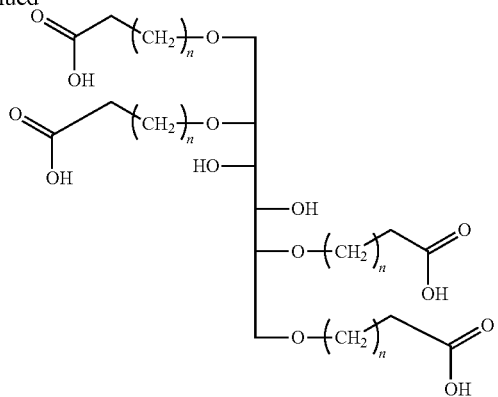

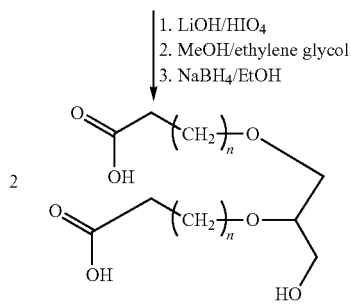

1.6 Diether Synthesis with ω-Hydroxycarboxylic Acid Esters and a 1,ω-Dibromoalkane with Subsequent Ester Cleavage

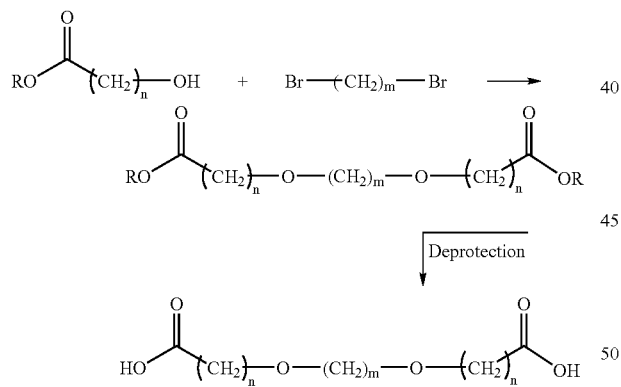

2. Dimerisation/Oligomerisation with an Extramembrane Spacer

The extramembrane spacer, because of its position outwith the biological membranes, must have predominantly hydrophilic properties. It has the following general structure:

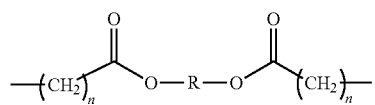

Examples of Synthesis Paths

2.1 Synthesis of Esters Made from Two Fatty Acid (s, Chlorides, Amides, Esters) with Bifunctional Compounds (Spacer Starting Molecules)

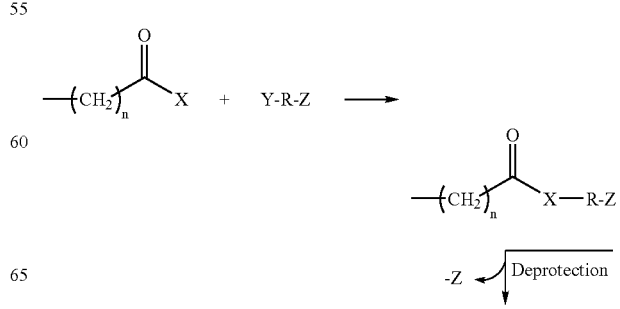

2.2 Step-Wise Cross-Linking to from Fatty Acid Diesters

2.2.0 General Reaction Diagram

21
-continued

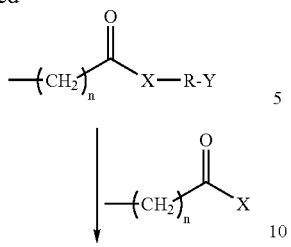

22
-continued

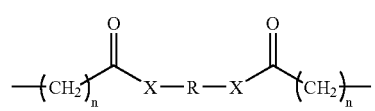

TABLE 1

Cross-linking molecules (spacer starting compounds) Y—R—Y with Y = OH, Cl, Br, NH₂, NHR,
OR' (alkane, alkene, alkine, arene) or with —O—, —N—, and with Z = as protective group (cf. Table 2)

| R | Y | Y—R—Y |
|---|---|---|
| (structure) | OH | N-acetyl-aspartic acid |
| (structure) | Cl, NH₂ | 1,3-dichloro-2-propanol<br>1,3-diamino-2-propanol |
| (structure) | OEt | diethylacetoamidomalonate |
| (structure) | OH | N-acetyl-glutamic acid |
| (structure) | (structure) | 2,3-O-isopropylidedene<br>1,4 di-O-tosyl D-threitol |
| (structure) | Br, OH | N,N'-dihydroxypropanyl-<br>2,3-isopropylidene-tatrate,<br>N,N'-dibromopropanyl-2,3-<br>isopropylidene-tatrate,<br>(from N,N'-diallyl-<br>tartaric acid-diamide |
| (structure) | NH₂ | D-2,3-diamino-propionic acid |

TABLE 1-continued

Cross-linking molecules (spacer starting compounds) Y—R—Y with Y = OH, Cl, Br, NH₂, NHR, OR' (alkane, alkene, alkine, arene) or with —O—, —N—, and with Z = as protective group (cf. Table 2)

| R | Y | Y—R—Y |
|---|---|---|
|  | NH₂ | oxalic acid dihydrazine |
|  | NH₂ | diamino-2,3-isopropylidene-butane |
|  | NH₂ | pentaethylenehexamine |
|  | NH₂ | 2,4-diamino-O-tosylbutyric acid ester |
|  | Cl | ethyleneglycol-bis-chloroacetate |
|  | OMe | dimethylglutaconate |
|  | OEt, Cl | ethyl-4-chloroacetoacetate |
|  | OH, Cl | tetraethyleneglycol |
|  | OH, Cl, NH₂ | triethyleneglycol 1,2-bis-(2-chloro-ethoxy)ethane 1,2-bis-(2-aminoethoxy)ethane |
|  | Cl | bis(2-chloroethyl)-ether |
|  | Cl | fumaric acid dichloride |
|  | OH, OMe | malic acid, dimethylmalate |
|  | OEt, OH | diethyl-3-oxoglutarate, 3-oxoglutaric acid |
|  | OEt | diethyl-3-hydroxy-glutarate |

TABLE 1-continued

Cross-linking molecules (spacer starting compounds) Y—R—Y with Y = OH, Cl, Br, NH$_2$, NHR, OR' (alkane, alkene, alkine, arene) or with —O—, —N—, and with Z = as protective group (cf. Table 2)

| R | Y | Y—R—Y |
|---|---|---|
| (structure) | | acetylene diurea |
| (structure) | NH$_2$ | bis-(tosyl-aspartic acid ester)-2-benzylglycol |
| (structure) | OH | bis-(N-boc-aspartic acid)-2 benzylglycol |
| (structure) | Cl | N,N'-(3-chloropropyryl)-urea |
| (structure) | Br | N,N'-(2-bromoisobutyryl)-urea |
| (structure) | Cl | N-(3-chloropropyryl)-2-hydroxy-glutarateamide |
| (structure) | Cl | 1,2-bis-[2-N-(3-chloropropyryl)-aminoethoxy)-ethane |
| (structure) | OMe | dimethyl-2-3-isopropylidenetatrate |
| (structure) | OH | mucic acid |

TABLE 1-continued

Cross-linking molecules (spacer starting compounds) Y—R—Y with Y = OH, Cl, Br, NH$_2$, NHR, OR' (alkane, alkene, alkine, arene) or with —O—, —N—, and with Z = as protective group (cf. Table 2)

| R | Y | Y—R—Y |
|---|---|---|
| (structure shown) | NH$_2$ | N,N'-(aspartic acid-benzylester)-urea |
| (structure shown) | NH$_2$, Br, Cl, OH | N,N'-(1-carboxy-5-amino propane)-urea, N,N'-(1-carboxy-5-bromo-propane)-urea, N,N'-(1-carboxy-5-chloro-propane)-urea, N,N'-(1-carboxy-5-hydroxy-propane)-urea |

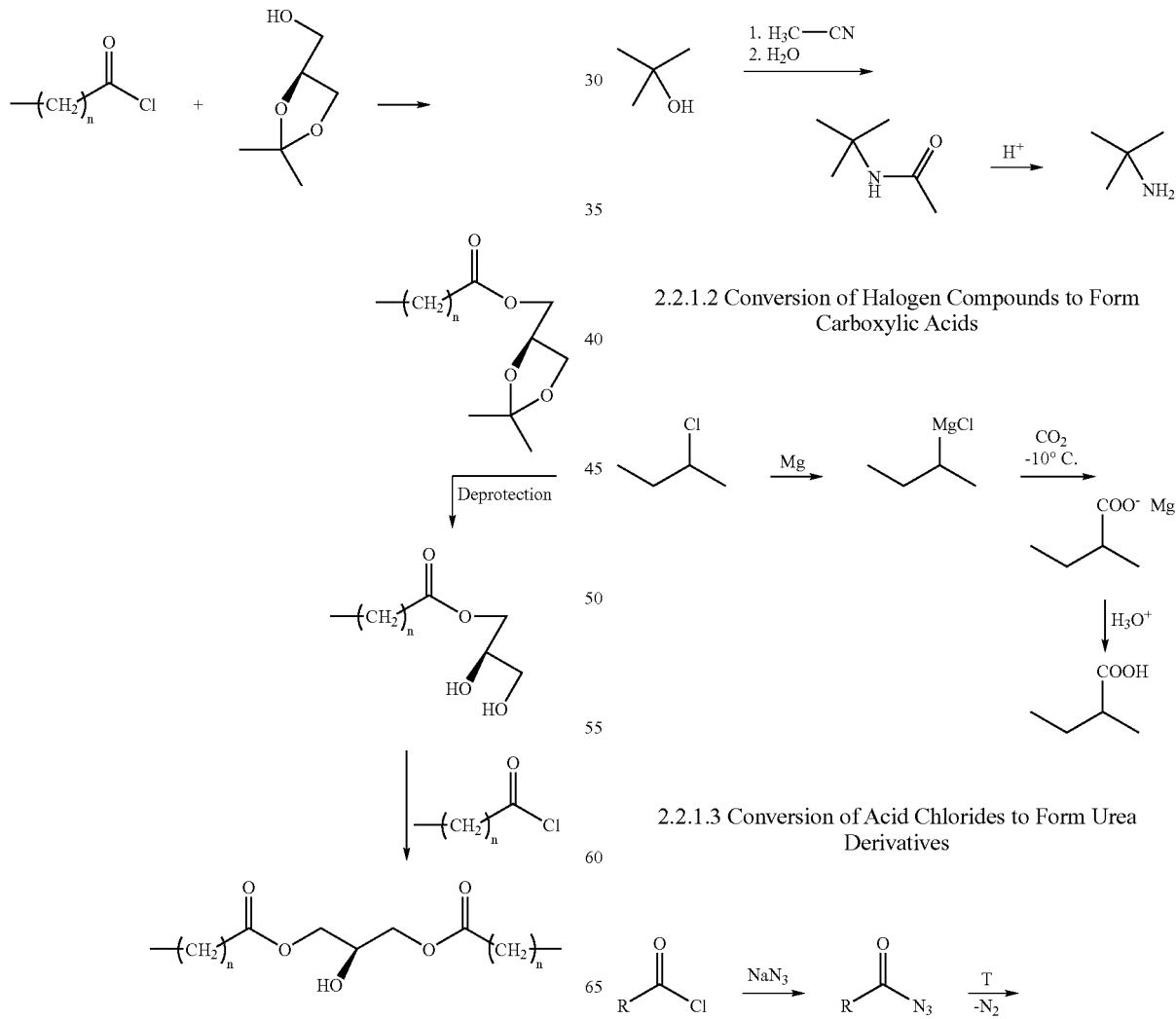

2.2.1 Reaction of an Acid Chloride with 2,3-Isopropylidene-sn-Glycerol

The subsequent reactions follow thereon:

2.2.1.1 Conversion of Alcohols to Form Amines

2.2.1.2 Conversion of Halogen Compounds to Form Carboxylic Acids

2.2.1.3 Conversion of Acid Chlorides to Form Urea Derivatives

-continued $$R-N=O \xrightarrow{R'NH_2} R\underset{H}{\overset{O}{\underset{\|}{N}}}NHR$$

2.2.1.4 Conversion of α-Ketone Acids to Form α-Amino Carboxylic Acids

[reaction scheme: boronic acid R¹B(OH)₂ + α-ketone acid R²C(O)COOH + amine R³R⁴NH → α-amino carboxylic acid with R¹, R², NR³R⁴, COOH]

2.2.2 Protective Groups

In the described synthesis reactions the compounds mentioned in Table 2 can be used as protective groups (Z).

TABLE 2

| Usable protective groups (Z): | |
|---|---|
| for alcohols: | |
| [structure] | Benzyl group |
| [structure] | THP group |
| [structure] | tert-butyldimethylsilyl group |
| [structure] | tert-butyldiphenylsilyl group |
| for amines: | |
| [structure] | Trifluoroacetate group |
| [structure] | Tosyl group |

TABLE 2-continued

| Usable protective groups (Z): | |
|---|---|
| [structure] | Boc group |
| [structure] | Fmoc group |
| [structure] | Trityl group |
| for carboxylic acids: | |
| [structure] | tert-butyl group |
| [structure] | Benzyl group |

The invention claimed is:

1. A cosmetic or body care agent, comprising a carrier suitable for cosmetic or body care applications and a dimer of at least two straight-chain and unbranched fatty acids, the fatty acids being bonded to each other covalently via their hydrophobic end by cross-linking of the respective ω-position carbon atoms of the fatty acid, the fatty acids being required to be bonded via a heteroatom-containing spacer, wherein the spacer is hydrophobic, and wherein at least one fatty acid is unsaturated.

2. A cosmetic or body care agent according to claim 1, wherein the fatty acids are, independently of each other, monocarboxylic acids with a chain length between 10 and 40 C-atoms.

3. A cosmetic or body care agent according to claim 2, wherein the fatty acids are selected from the group consisting of palmitic acid, lauric acid, myristic acid, stearic acid, arachidic acid, lignoceric acid, palmitoleic acid, oleic acid, 9,11-octadecadienoic acid ($C_{17}H_{31}$—COOH), linoleic acid, linolenic acid, 5,8,11,14,17-icosapentaenoic acid, 4,7,10,13, 16,19-docosahexaenoic acid, cerebronic acid, decanoic acid, octacosanoic acid and 9-octacosenoic acid.

4. A cosmetic or body care agent according to claim 1, wherein the spacer comprises one or more oxygen- or nitrogen atoms.

5. A cosmetic or body care agent according to claim 1, wherein at least one fatty acid is saturated.

6. A cosmetic or body care agent according to claim 1, wherein the fatty acids are of a natural origin.

7. A human or veterinary drug containing a cosmetic or body care agent according to claim 1.

8. A cosmetic or body care agent according to claim 1, wherein the fatty acids are of a semi-synthetic or synthetic origin.

* * * * *